(12) United States Patent
Weber

(10) Patent No.: US 8,449,803 B2
(45) Date of Patent: May 28, 2013

(54) METHOD OF FORMING A CATHETER

(75) Inventor: Jan Weber, Maastricht (NL)

(73) Assignee: Boston Scientific Scimed, Inc., Maple Grove, MN (US)

(*) Notice: Subject to any disclaimer, the term of this patent is extended or adjusted under 35 U.S.C. 154(b) by 34 days.

(21) Appl. No.: 13/040,099

(22) Filed: Mar. 3, 2011

(65) Prior Publication Data

US 2011/0148003 A1 Jun. 23, 2011

Related U.S. Application Data

(62) Division of application No. 11/818,021, filed on Jun. 13, 2007.

(51) Int. Cl.
*B29C 41/22* (2006.01)

(52) U.S. Cl.
USPC ........... 264/255; 264/483; 264/447; 264/496; 264/313; 264/334

(58) Field of Classification Search
None
See application file for complete search history.

(56) References Cited

U.S. PATENT DOCUMENTS

| | | | |
|---|---|---|---|
| 3,941,858 A | 3/1976 | Shepherd et al. | |
| 4,536,179 A * | 8/1985 | Anderson et al. | 604/266 |
| 4,636,346 A * | 1/1987 | Gold et al. | 264/139 |
| 4,840,623 A * | 6/1989 | Quackenbush | 604/524 |
| 4,874,373 A * | 10/1989 | Luther et al. | 604/164.03 |
| 4,955,862 A | 9/1990 | Sepetka | |
| 5,143,089 A | 9/1992 | Alt | |
| 5,411,527 A | 5/1995 | Alt | |
| 5,433,730 A | 7/1995 | Alt | |
| 5,474,797 A | 12/1995 | Sioshansi et al. | |
| 5,507,760 A | 4/1996 | Wynne et al. | |
| 5,520,664 A | 5/1996 | Bricault, Jr. et al. | |
| 5,531,715 A * | 7/1996 | Engelson et al. | 604/265 |
| 5,670,111 A * | 9/1997 | Conway et al. | 264/512 |
| 5,830,329 A | 11/1998 | Stewart et al. | |
| 5,971,954 A * | 10/1999 | Conway et al. | 604/101.05 |
| 6,168,580 B1 | 1/2001 | Yardley | |
| 6,254,552 B1 | 7/2001 | Lewis et al. | |
| 6,383,434 B2 * | 5/2002 | Conway et al. | 264/221 |
| 6,400,992 B1 | 6/2002 | Borgersen et al. | |
| 6,434,430 B2 | 8/2002 | Borgersen et al. | |
| 6,623,521 B2 | 9/2003 | Steinke et al. | |
| 6,638,569 B2 | 10/2003 | McLaughlin et al. | |

(Continued)

FOREIGN PATENT DOCUMENTS

| | | |
|---|---|---|
| DE | 10 2004 061 183 | 7/2006 |
| EP | 1 090 656 | 4/2001 |
| GB | 2 009 359 | 6/1979 |
| WO | 2007/022174 | 2/2007 |

OTHER PUBLICATIONS

International Search Report. Dec. 12, 2008. 6 pgs.

(Continued)

*Primary Examiner* — Edmund H. Lee
(74) *Attorney, Agent, or Firm* — Brooks, Cameron & Huebsch, PLLC

(57) ABSTRACT

Apparatuses, systems, and methods for surface modification of catheters. The surface modification can be localized to a lumen surface of the catheter. The surface modification to the lumen surface extends radially into the catheter body a predetermined distance to provide a hardened zone having a hardness that is greater than a hardness of an exterior surface of the catheter body.

15 Claims, 7 Drawing Sheets

U.S. PATENT DOCUMENTS

| | | |
|---|---|---|
| 6,759,431 B2 | 7/2004 | Hunter et al. |
| 6,761,736 B1 | 7/2004 | Woo et al. |
| 6,824,559 B2 | 11/2004 | Michal |
| 6,960,215 B2 | 11/2005 | Olson, Jr. et al. |
| 7,056,523 B1 | 6/2006 | Claude et al. |
| 7,112,298 B2 * | 9/2006 | Kampa et al. ............ 264/301 |
| 2001/0027310 A1 * | 10/2001 | Parisi et al. ............ 604/524 |
| 2002/0026899 A1 | 3/2002 | McLaughlin et al. |
| 2003/0083231 A1 | 5/2003 | Ahlem et al. |
| 2003/0125712 A1 | 7/2003 | Zhou |
| 2003/0181935 A1 | 9/2003 | Gardeski et al. |
| 2003/0212426 A1 | 11/2003 | Olson, Jr. et al. |
| 2004/0210289 A1 | 10/2004 | Wang et al. |
| 2004/0231926 A1 * | 11/2004 | Sakhrani et al. ............ 184/18 |
| 2004/0249382 A1 | 12/2004 | Olson, Jr. et al. |
| 2004/0254419 A1 | 12/2004 | Wang et al. |
| 2005/0025797 A1 | 2/2005 | Wang et al. |
| 2005/0048121 A1 | 3/2005 | East et al. |
| 2005/0079132 A1 | 4/2005 | Wang et al. |
| 2005/0107870 A1 | 5/2005 | Wang et al. |
| 2005/0153379 A1 | 7/2005 | Hoon et al. |
| 2005/0155779 A1 | 7/2005 | Wang et al. |
| 2005/0182482 A1 | 8/2005 | Wang et al. |
| 2005/0187268 A1 | 8/2005 | Von Rechenberg et al. |
| 2005/0197689 A1 | 9/2005 | Molaei |
| 2005/0240100 A1 | 10/2005 | Wang et al. |
| 2005/0244337 A1 | 11/2005 | Wange et al. |
| 2005/0261763 A1 | 11/2005 | Wang et al. |
| 2005/0278020 A1 | 12/2005 | Wang et al. |
| 2006/0079492 A1 | 4/2006 | Ahlem et al. |
| 2006/0089608 A1 | 4/2006 | Shaykh et al. |
| 2006/0142853 A1 | 6/2006 | Wang et al. |
| 2006/0157159 A1 | 7/2006 | Yeung et al. |
| 2006/0200226 A1 | 9/2006 | Furst et al. |
| 2007/0010702 A1 | 1/2007 | Wang et al. |
| 2007/0027532 A1 | 2/2007 | Wang et al. |

OTHER PUBLICATIONS

Lauer, J.L., et al. "Reduced Adhesion of human bloodplatelets to polyethylene tubing by microplasma surface...", J. Appl. Phys., vol. 96, No. 8, pp. 4539-4346 (Oct. 15, 2004).

Shohet, J.L., et al., "Plasma Discharge in "Artificial Blood Vessels"", http://pptlengr.wisc.edu/publications/abstract_HeM1L1_3843.htm (2001).

Zhang, Gu-Lin, et al., "inner Surface Modification of the Tube Materials...", Oral Session, Modification of Material Properties, 100080 pp. 251-254 (date unknown).

* cited by examiner

METHOD OF FORMING A CATHETER

CROSS-REFERENCE TO RELATED APPLICATIONS

This application is a divisional of U.S. patent application Ser. No. 11/818,021, filed Jun. 13, 2007 still pending, which is herein incorporated by reference.

TECHNICAL FIELD

The present disclosure relates generally to catheters, and more particularly to catheters having modified surfaces.

BACKGROUND

Friction encountered between wires and catheter lumen surfaces or between catheters and the inside of the lumen of guiding catheters provides a significant hurdle in the ability to smoothly steer and rotate the wires and/or catheters inside of the human body. A suitable approach to address this problem is needed.

DETAILED DESCRIPTION

Figure 1:
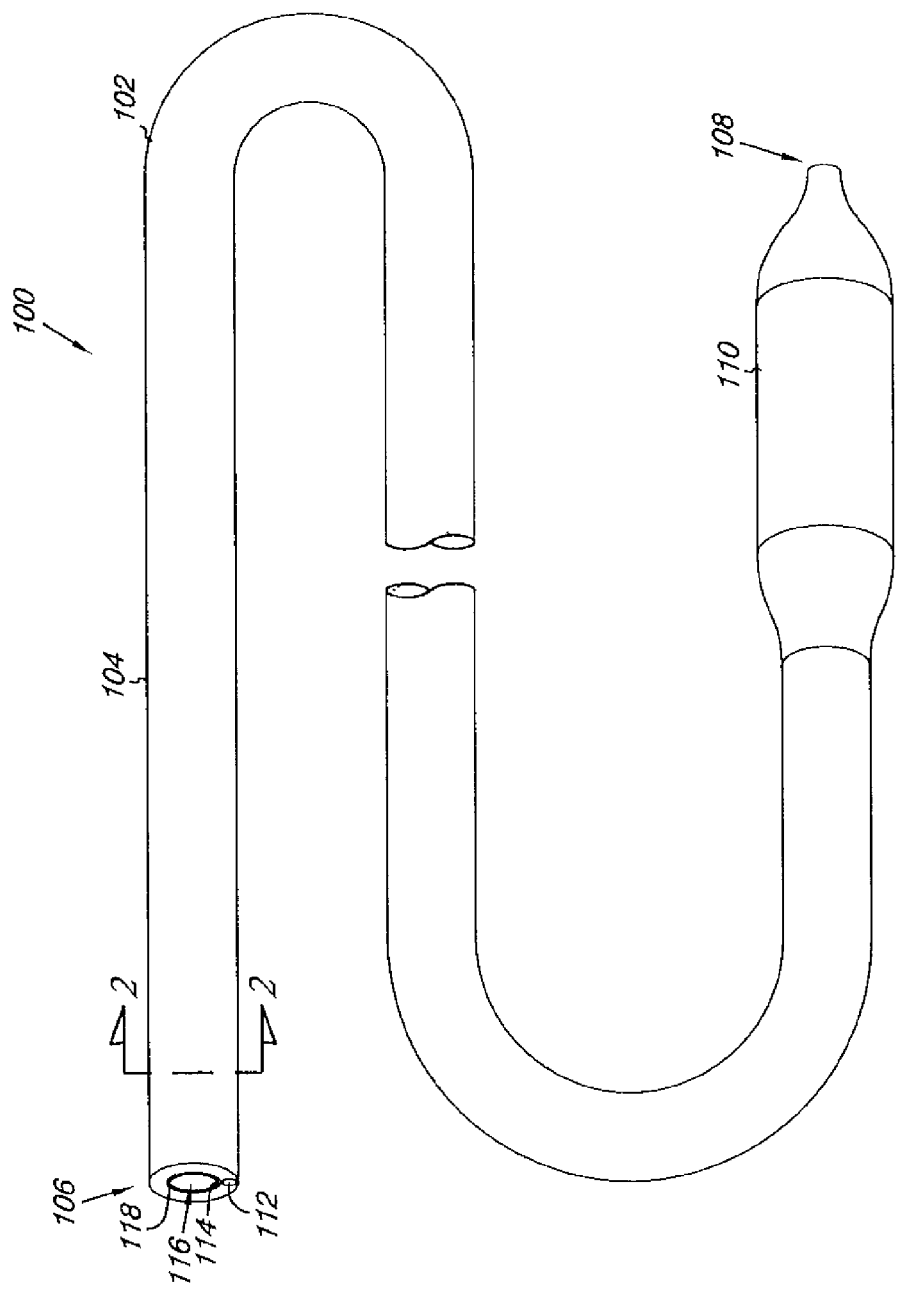
FIG. 1 illustrates an embodiment of a catheter having a lumen surface with a hardened zone according to the present disclosure.

Embodiments of the present disclosure are directed to apparatuses, systems, and methods for surface modification of catheters. For the various embodiments, the surface modification can be localized to a lumen surface of the catheter. The surface modification to the lumen surface extends radially into the catheter body a predetermined distance to provide a hardened zone.

As used herein, a "hardened zone" includes a region of the material forming at least a portion of the catheter that extends from the lumen surface toward an exterior surface of the catheter, where the material in the region of the hardened zone has undergone at least a partial modification from energy delivered by ions driven into the elongate body according to the methods of the present disclosure. For the various embodiments, the hardened zone can provide either a non-discrete or discrete layer resulting from a change to the material forming the catheter.

For the various embodiments, the catheter includes a polymeric elongate body that is subjected to at least a partial modification by an ion treatment discussed herein. The ion treatment of the present disclosure can result in the formation of a high level of macromolecule defects in a thin surface layer of the catheter material to form the hardened zone. For the various embodiments, the macromolecule defects cause structure transformations of the polymer chains through chemical reactions of free radicals formed by the ions, which can cause the formation of the hardened zone.

As used herein, a "modification" of the polymer chains forming the polymeric elongate body includes disrupting and recombining carbon-carbon bonds of the polymeric material to form structures ranging from amorphous carbon, fully carbonized or graphitized, partially carbonized to diamond like structures.

In addition, the thickness of the hardened zone can correspond to the distribution of defects which are determined by the energy and the kind of ions and/or the kind of polymer used in forming the polymer elongate body. The depth of the modification can be from several tens of nanometers to hundreds of nanometers, as will be discussed herein.

As used herein, the terms "a," "an," "one or more," and "at least one" are used interchangeably. In addition, it is recognized that the surface modification of the present disclosure is not limited to lumen surfaces and can be used on other areas and/or regions of a catheter in addition to the lumen surface.

Unless otherwise indicated, all numbers expressing quantities of ingredients, processing conditions, and so forth used in the disclosure and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, each numerical parameter should at least be construed in light of the number of reported significant digits and by applying ordinary rounding techniques.

For the various embodiments, the hardened zone formed at and extending from the lumen surface results in a surface having a material hardness that is greater than the material hardness of other polymer regions of the catheter body. For the various embodiments, the hardened zone can be formed from the polymeric material that forms (i.e., constitutes) the unmodified catheter (i.e., the catheter before surface modification according to the present disclosure). In other words, the hardened zone is formed in the polymeric material forming the catheter body, as apposed to being applied to polymeric material of the catheter body.

For the various embodiments, the hardened zone of the present disclosure provides for reduced contact frictional forces between the lumen surface and an item being moved relative thereto (e.g., through the lumen) as compared to an unmodified catheter. Such items can include, but are not limited to guidewires, balloon catheters, enclosed self-expanding stents, surgical instruments guided through endoscopic catheters or urological catheters (such as kidney stone retrieval baskets), and/or additional catheters. In addition, the presence of the hardened zone does not significantly, if at all, affect the bulk physical properties of the catheter as compared to an unmodified catheter. In other words, a catheter having the hardened zone according to the present disclosure display essentially the same bulk mechanical properties (e.g., stiffness, elongation at breaking, modulus of elasticity, tensile strength, stress-strain response, flexibility, etc.) as an identical catheters not having the hardened zone of the present disclosure. In addition, the hardened zone also resists sloughing or flaking of the polymeric material that forms the hardened zone.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide any number of additional embodiments of the present disclosure. In addition, as will be appreciated the proportion and the relative scale of the elements provided in the figures are intended to illustrate the embodiments of the present invention, and should not be taken in a limiting sense.

FIG. 1 provides an embodiment of a catheter 100 according to the present disclosure. The catheter 100 includes a polymer elongate catheter body 102 having an exterior surface 104 that extends from a first end 106 to a second end 108. As illustrated, the catheter 100 further includes an inflatable balloon 110 positioned around the catheter 100. An inflation lumen 112 extends from the first end 106 of the polymer elongate catheter body 102 to be in fluid communication with an interior chamber of the inflatable balloon 110 to allow the balloon 110 to be inflated and deflated.

The catheter 100 further includes a lumen surface 114 that defines a lumen 116. In one embodiment, the lumen 116 extends from the first end 106 to the second end 108. Alternatively, the lumen 116 can extend from the first end 106 to a location between the first and second ends 106 and 108.

The catheter 100 further includes a hardened zone 118 according to the present disclosure. For the present embodiments, the hardened zone 118 originates from the polymer structure forming the polymer elongate catheter body 102 through the modification processes described herein. In one embodiment, the hardened zone 118 of the lumen surface 114 can be a continuous surface of the modified polymeric material. Alternatively, the hardened zone can have a discontinuous surface with a predefined pattern, as will be discussed more fully herein.

In one embodiment, the hardened zone 118 extends radially into the polymer elongate catheter body 102 from the lumen surface 114 to a predetermined depth. For the various embodiments, the predetermined depth of the hardened zone 118 can be from about 2 nanometers to about 400 nanometers. Alternatively, the thickness or depth of the hardened zone 118 can be from about 20 nanometers to about 200 nanometers, or from about 100 nanometers to about 200 nanometers. Alternatively, expressed as a percentage, the predetermined depth can have a value of 0.05 percent (%) through 10 percent (%) of the average wall thickness of the polymer elongate catheter body 102.

For the various embodiments, the hardened zone 118 can have a material hardness value ranging from 1 Gpa (e.g., when formed from polymers having a high ratio of $sp^2/sp^3$ hybrid bonds) to 40 Gpa (e.g., when formed from polymers having mainly $sp^3$ bonds). Measurements of the hardened zone 118 can be made using a Nano-Hardness Tester, for example from CSM Instruments Inc. (Needham, Mass., USA). The Nano-Hardness Tester is specially suited to load and penetration depth measurements at nanometer length scales. The Nano-Hardness Tester(s) can also be used in the analysis of organic and inorganic soft and hard coatings.

For the various embodiments, the material hardness of the hardened zone can be uniform through its predetermined depth. Alternatively, the hardened zone 118 can have a material hardness value (e.g., 5.30 Gpa) that changes (e.g., decreases) in value from the lumen surface 114 through its predetermined depth. In addition, the thickness of the hardened zone 118 has little to no measurable effect on the bulk mechanical properties (e.g., stiffness, elongation at breaking, modulus of elasticity, tensile strength, stress-strain response, flexibility, etc.) of the polymer elongate catheter body 102.

Figure 2:
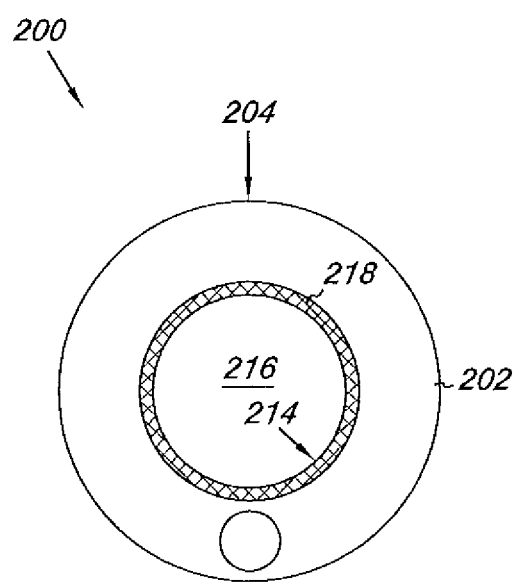
FIG. 2 illustrates a cross sectional view of the catheter of FIG. 1 taken along lines 2-2 according to one embodiment of the present disclosure.

FIG. 2 provides a cross-sectional view of the catheter 100 taken along the lines 2-2 in FIG. 1. According to the embodiment illustrated in FIG. 2, the hardened zone 218 extends into the elongate body 202 from the lumen surface 214. For the various embodiments, the hardened zone 218 can gradually transition from, for example, a carbonized region at the lumen surface 214 through a partially carbonized region of the polymeric material to a deeper unaffected polymeric material of the polymer elongate catheter body 202.

In one embodiment, variation in the depth of the hardened zone 218 can be attributed to the surface modification process of the present disclosure in which ions are driven into the lumen surface 214 of the polymer elongate catheter body 202. Depending on the energy of the ions being driven into the lumen surface 214, the polymeric bonds of the polymer elongate catheter body 202 are disrupted and recombine as carbon-carbon structures, ranging from amorphous carbon to diamond like structures, up to a depth of several tens or hundreds of nanometers, as discussed herein. The resulting hardened zone 218 has a surface with a material hardness that is greater than both a hardness of the lumen surface before the surface modification and the exterior surface 204 of the polymer elongate catheter body 202.

The carbonization and oxidation processes discussed herein can be observed in a variety of polymers. Suitable polymer include, block co-polymers of polyamide and polyether sold under the trade designator Pebax, nylons, polyurethanes, polyamides, polyethylene, silicone, latex, polyethylene terephthalate or other polyesters, polyvinylchloride, etc. More generally, polymers having a high content of carbon-carbon bonds are also suitable.

Referring back to FIG. 1, the lumen 116 is configured to receive and pass a guidewire for guiding and positioning the catheter 100 in the vasculature. In one embodiment, the hardened zone 118 allows for a reduced coefficient of friction (e.g., static and kinetic fiction) between the lumen surface 114 and the guidewire as compared to an unmodified lumen surface of the same polymer elongate body under the same conditions (e.g., temperature, relative speed of the guidewire and catheter, the contact geometry the guidewire and catheter experience).

As will be appreciated, the hardened zone as discussed herein can be created in a number of different types of catheters. One example is the balloon catheter 100 illustrated in FIG. 1. Other examples include, but are not limited to, coronary guide catheters that can be used to pass guidewires and/or balloon catheters, including balloon catheters with a stent mounted thereto. An addition example includes a catheter or sheath used in holding, moving and/or delivering a self-expanding stent to an implant location in the body.

Other applications for the present disclosure can include surface modification of lumens in cardiac leads, such as pacing leads and/or defibrillation leads. In addition, surface modification according to the present disclosure can be used with a lumen surface of a medical device that has a small inner diameter (e.g., I.D. of 5 mm or less), which would benefit from a reduction in a coefficient of friction between the lumen of the medical device and one or more other structures that come in contact with the lumen.

Figure 3:
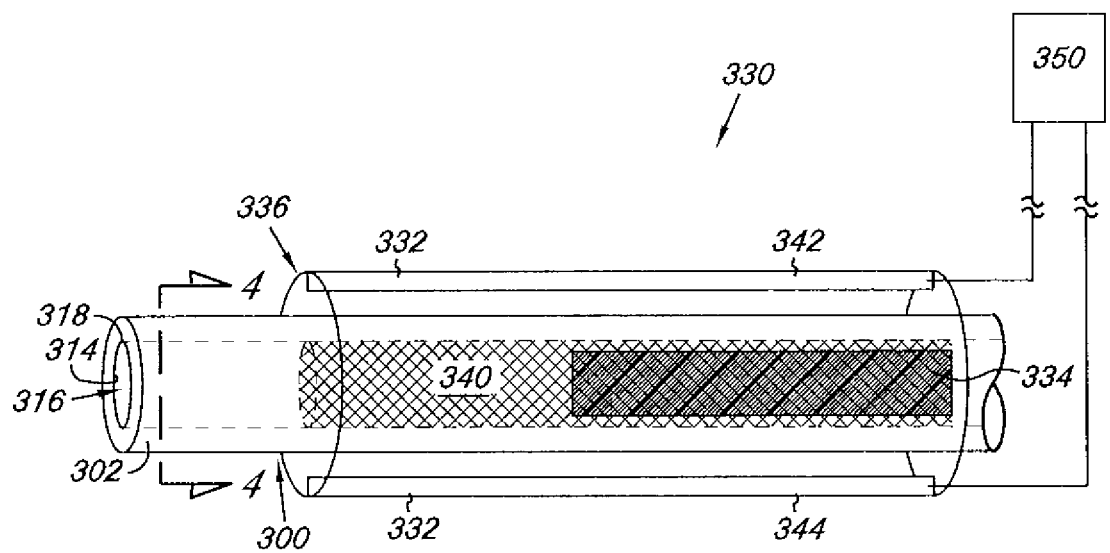
FIG. 3 illustrates an apparatus for the surface modification of a lumen surface of a catheter according to one embodiment of the present disclosure.

FIG. 3 provides an illustration of an apparatus 330 for the surface modification of the catheter 300 as discussed herein. In one embodiment, the apparatus 330 can modify the catheter 300 by driving ions into the catheter 300. One example of driving ions into the catheter 300 can be through a Plasma Ion Immersion Implantation (PIII), in which high energetic ions (5-40 keV) are driven into the polymer surface of the catheter 300. As discussed herein, this surface modification produces the hardened zone 318 of the present disclosure in the catheter 300.

As illustrated, the apparatus 330 includes a first pair of plasma electrodes 332 and a second pair of implanting electrodes 334 positioned outside, around and adjacent to the exterior surface 304 of the polymer elongate body 302. The apparatus 330 further includes a housing 336 positioned around the plasma electrodes 332 and the implanting electrodes 334. In one embodiment, the housing 336 is formed of an electrically insulating material to better direct energy from the electrodes 332 and 334 across the elongate body 302 of the catheter 300. Examples of such materials include, but are not limited to, glass and polytetrafluoroethylene (PTFE). Other electrically insulating materials are known and could be used for the housing 336.

For the various embodiments, the plasma generating electrodes 332 can be used to create a plasma 340 of ions inside the lumen 316 of the catheter 300. In one embodiment, the plasma electrodes 332 can include a cathode 342 and an anode 344 positioned in an opposing configuration across the catheter 300. For the various embodiments, the catheter 300 can be feed through the apparatus 330 past the electrodes 332, where the electrodes 332 and the housing 336 are in close proximity to the exterior surface 304 of the elongate body 302 so as to prevent the formation of plasma outside the lumen 316.

For the various embodiments, the plasma electrodes 332 can be used to provide RF energy to a plasma gas being streamed through the lumen 316 to generate the plasma 340 inside of the lumen 316. In one embodiment, the plasma gas can include one or more of nitrogen ($N_2$), argon (Ar), xenon (Xe), helium (He), oxygen ($O_2$) and/or combinations thereof. For the various embodiments, the plasma gas can be streamed through the lumen 316 at a pressure in the range of $10^{-3}$ Pa through $10^{-1}$ Pa.

To generate the plasma 340, the plasma electrodes 332 can be operatively connected to a radiofrequency generator 350. For the various embodiments, the radiofrequency generator 350 can provide power at a desired frequency to the electrodes 332 to generate the plasma 340. For the various embodiments, the radiofrequency generator 350 can apply RF energy pulses at a predetermined frequency (i.e., a pulse repetition frequency) of 0.2 Hz to 200 Hz. In one embodiment, pulsing the RF energy helps to prevent overheating of the polymer elongate body 302 of the catheter 300 during the surface modification techniques in producing the hardened zone. In addition, the radiofrequency generator 350 can deliver RF energy through the electrodes 332 at peak voltages in the range of 5 to 40 keV. Specific examples of such peak voltages include, but are not limited to, 5, 10, 20 and 30 keV.

The ions from the plasma 340 can then be driven into the lumen surface 314 using the second pair of implanting electrodes 334. For example, the second pair of implanting electrodes 334 can be used to accelerate and drive the ions from the plasma 340 into the wall of the lumen surface 314 to form the hardened zone 318 described herein.

In one embodiment, the implanting electrodes 334 can be used to deliver alternating negative and positive voltage pulses at a voltage of 20 to 40 keV across the implanting electrodes 334 at the predetermined frequency to accelerate and drive the ions from the plasma 340 into the wall of the lumen surface 314. For the various embodiments, the predetermined frequency can have a value of 100 to 600 Hz. For the various embodiments, this allows for doses of ions delivered from the plasma 340 to the lumen surface 314 to be from $5 \times 10^{14}$ through $10^{17}$ ions/cm$^2$, where doses of $10^{16}$ ions/cm$^2$ or higher are also suitable.

The operating parameters of the apparatus 330 discussed herein can be used to form different configurations of the hardened zone 318 in the polymer elongate body 302. For example, the operating parameters can be used to create the hardened zone 318 that gradually transitions from one or more of an amorphous carbon, fully carbonized or graphitized, partially carbonized to diamond like surface to a non-hardened zone in the polymer elongate catheter body 302. In addition, the operating parameters can be used to control the depth, or thickness, of the hardened zone 318, as discussed herein, to maintain bulk mechanical properties of the polymer elongate catheter body 302.

For the various embodiments, the relative size and position of the plasma electrodes 332 and the implanting electrodes 334 can be configured to better maintain the stability of the plasma 340 inside the lumen 316 of the polymer elongate catheter body 302. In some situations the implanting electrodes 334 can disrupt the plasma 340 as they drive the ions into the elongate body 302. In one embodiment, the plasma electrodes 332 can extend past the implanting electrodes 334 upstream relative the direction of plasma gas flow to better maintain and supply the plasma 340 to the region of the implanting electrodes 334. For the various embodiments, the plasma electrodes 332 can be at least twice as long as the implanting electrodes 334 as measured in the direction of the longitudinal axis of the elongate body 302.

In addition embodiment, the supply of the plasma 340 formed with the plasma electrodes 332 can also be dependent upon both the flow rate of the plasma gas and the pulse frequency of the RF energy used to form the plasma 340. For example, the flow rate of the plasma gas and the pulse frequency of RF energy delivered from the plasma electrodes 340 can be adjusted so as to ensure that enough plasma gas is supplied between pulses to allow for more plasma 340 to be formed. As a result, the faster the pulse frequency of the RF energy, the faster the flow rate of the plasma gas may need to be.

In an additional embodiment, to better ensure the surface modification treatment of the present disclosure treats the entire lumen surface 314 of the elongate body 302, one or both of the electrodes 332 and 334 and/or the catheter 300 can be rotated relative each other around the longitudinal axis of the catheter 300. Also, to treat longer sections of catheters 300, the elongate body 302 can be feed past the electrodes 332 and 334 via a reel-to-reel system.

Figure 4:
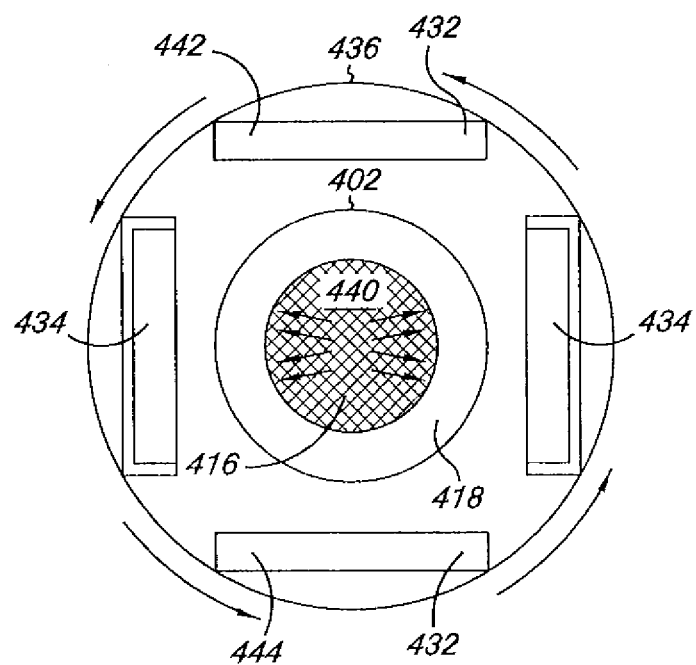
FIG. 4 illustrates a cross sectional view of the apparatus and the catheter of FIG. 3 taken along lines 4-4 according to the present disclosure.

FIG. 4 provides a cross-sectional view of the apparatus 330 taken along the lines 4-4 in FIG. 3. As illustrated, the electrodes 432 and 434 and the housing 436 can rotate relative the elongate body 402 of the catheter 400, or visa versa, to better ensure the ions being driven by the implanting electrode 434 are exposure around the lumen surface 414. In an additional embodiment, both the apparatus 430 and the elongate body 402 can be rotated in opposite directions simultaneously.

FIGS. 5A-5D provide an additional embodiment of the catheter 500 according to the present disclosure. As discussed herein, the catheter 500 illustrates an embodiment in which the hardened zone 518 is formed as a discrete layer relative the remaining portions of the catheter 500. In one embodiment, the hardened layer 518 can be formed having a uniform hardness value through the thickness of the hardened layer 518.

Figure 5A:
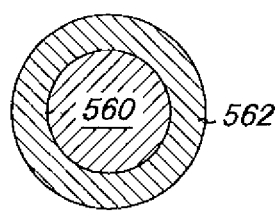
FIGS. 5A-5D illustrate the formation of a catheter having a hardened zone according to one embodiment of the present disclosure.

For the various embodiments, a layer 562 of a first polymer material can be deposited on a mandrel 560, as illustrated in FIG. 5A. For the various embodiments, the mandrel 560 can be an electrically conductive, flexible, ductile, metal or a metal alloy. Examples of suitable materials for the mandrel 560 include, but are not limited to, copper, brass, zinc, and PTFE coated soft metallic alloys.

In one embodiment, the first polymer material can be one or more of the polymers discussed herein. As will be appreciated, depositing the first polymer material on the mandrel 560 can be accomplished by a number of different coating techniques. Such techniques include, but are not limited to, spray coating, ultrasonic mist coating, dip coating, electrostatic coating, over-extrusion techniques and/or printing or patterning the polymer layer 562 on the mandrel 560. Other coating techniques are also possible.

In one embodiment, the resulting polymer layer 562 can have a thickness of about 2 nanometers to about 400 nanometers, from about 20 nanometers to about 200 nanometers, or from about 100 nanometers to about 200 nanometers. Other thicknesses are also possible.

Figure 5B:
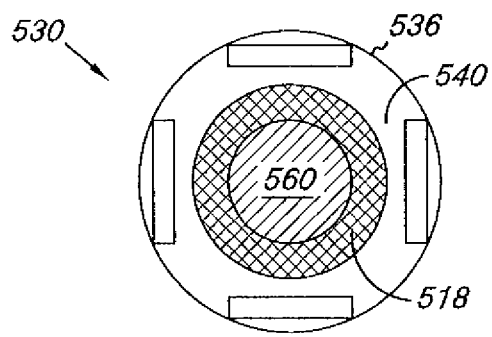

FIG. 5B provides an illustration of the mandrel 560 with its polymer layer 562 being fed through the apparatus 530 to form the hardened zone 518 in at least a portion of the first polymer material. As discussed herein, the apparatus 530 includes the housing 536, the plasma electrodes 532 for generating the plasma 540 and the implanting electrodes 534 for driving the ions into the polymer layer 562.

For the present embodiment, the mandrel 560 can be formed of an electrically conductive material to allow the mandrel 560 to be used as a pole (e.g., a cathode) in delivering alternating negative and positive voltage pulses, as discussed herein, for driving the ions into the polymer layer 562. The result can be the formation of the hardened zone 518 from the polymer layer 562. For the various embodiments, the entire polymer layer 562 can be formed into the hardened zone 518, as discussed here. Alternatively, less than the entire polymer layer 562 can be formed into the hardened zone 518, as will be more fully discussed herein.

For the various embodiments, the plasma gas, as discussed herein, used in forming the plasma 540 can be supplied between the electrodes 532, 534 and the polymer layer 562. For the various embodiments, the flow rate of the plasma gas can be dependent upon the frequency of the RF pulses delivered from the plasma electrodes 532 and the desire to maintain a stable plasma 540.

As discussed herein, the apparatus 530 and/or the mandrel 560 with the polymer layer can rotate relative the other or relative each other. In addition, the electrodes 532 and 534 can have the same proportional and configurational relationship as discussed herein (e.g., the plasma electrodes 532 being longer than the implanting electrodes 534).

Figure 5C:
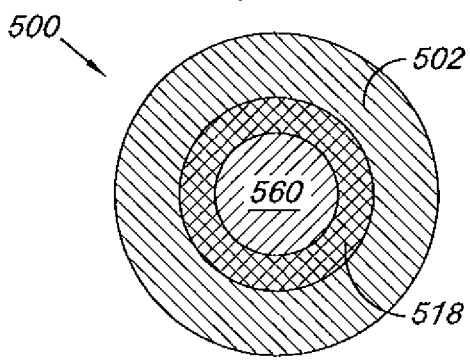
Figure 5D:
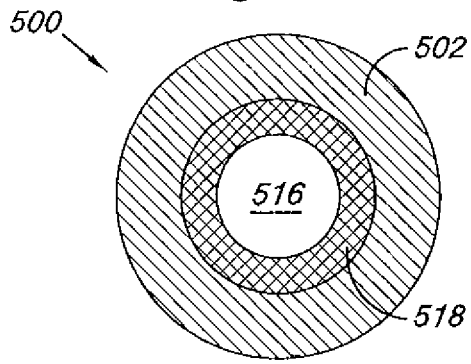

FIG. 5C next illustrates the hardened layer 518 formed over the mandrel 560 being coated with one or more layers of a second polymer material to form the catheter 500. In one embodiment, the second polymer material can be the same type of polymer used to form the polymer layer 562 and/or a different polymer to form the polymer elongate body 502 of the catheter 500. The polymer(s) used in the coating process can include those provided herein. Alternatively, other polymer and/or non-polymer materials can be used in coating the hardened zone 518 formed on the mandrel 560.

In one embodiment, the coating process can be applied through an over-extrusion process. Alternatively, the coating process can be a can be a dip coating technique. Other coating processes discussed herein are also possible. The mandrel 560 can then be removed from the catheter 500 by axially stretching the mandrel 560 so as to reduce its diameter and allow it to be separated and removed from the catheter 500.

FIG. 6A-6D provides an additional embodiment of the catheter 600 according to the present disclosure. As discussed herein, the catheter 600 illustrates an embodiment in which the hardened zone 618 is formed as a discrete layer relative the remaining portions of the catheter 600.

Figure 6A:
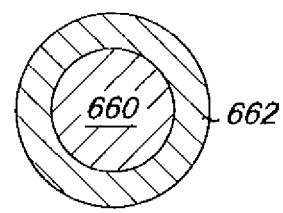
FIGS. 6A-6D illustrate the formation of a catheter having a hardened zone according to one embodiment of the present disclosure.

As illustrated in FIG. 6A, the mandrel 660 can be coated with the layer 662 of the first polymer material, as discussed herein, by one or more of the coating techniques discussed herein. The resulting polymer layer 662 can have a thickness sufficient to allow a portion of the polymer layer 662 to be converted into the hardened zone 618 while leaving at least a portion of the polymer layer 662 between the hardened zone 618 and the mandrel 660. Examples of suitable thicknesses include, but are not limited to, about 300 nanometers to about 600 nanometers.

Figure 6B:
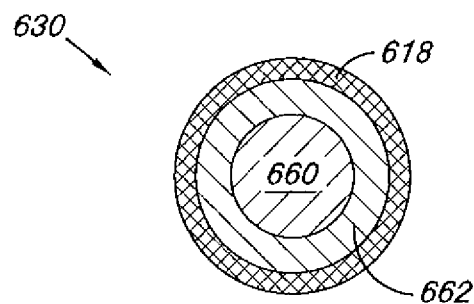

FIG. 6B provides an illustration of the mandrel 660 with its polymer layer 662 after being fed through the apparatus, as discussed herein, to transform at least a portion of the polymer layer 662 into the hardened zone 618. For the present embodiment, the ion and implant energy used with the plasma and implanting electrodes can be selected to be such that the portion of the polymer layer 662 from the exterior surface toward the mandrel 660 is transformed (e.g., carbonized) into the hardened layer 618. As illustrated in FIG. 6B, the result is a region of the polymer layer 662 positioned between the hardened layer 618 and the mandrel 660.

Figure 6C:
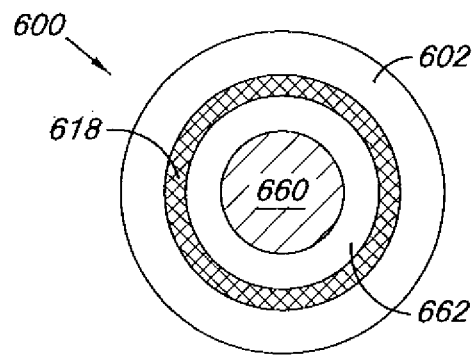

FIG. 6C next illustrates the hardened layer 618 being coated with one or more layers of the same polymer used to form the polymer layer 662 and/or a different polymer to form the polymer elongate body 602 of the catheter 600. The polymer(s) used in the coating process can include those provided herein. Alternatively, other polymer and/or non-polymer materials can be used in coating the hardened zone 618. In one embodiment, the coating process can be applied through one or more processes discussed herein.

Figure 6D:
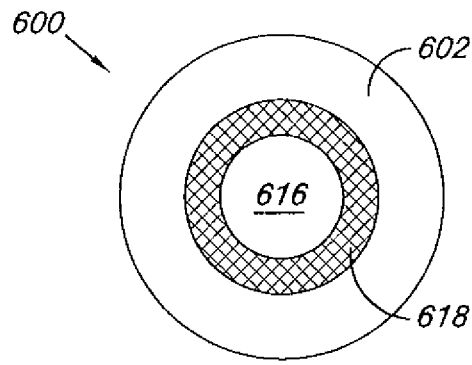

A solvent can then be used to dissolve the first polymer material of the layer 662 to both expose the hardened zone 618 and release the mandrel 660 from the catheter 600, as illustrated in FIG. 6D. Selection of a suitable solvent will depend upon the polymer(s) used in forming the polymer layer 662.

Figure 7A:
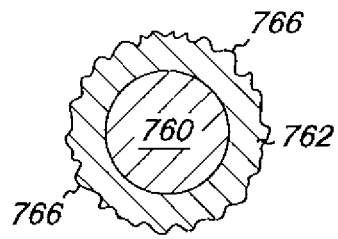
FIGS. 7A-7D illustrate the formation of a catheter having a hardened zone according to one embodiment of the present disclosure.

FIGS. 7A-7D provide a further illustration of the catheter 700 according to the present disclosure. As discussed herein, the catheter 700 illustrates an embodiment in which the hardened zone 718 is formed as a non-uniform continuous layer. As illustrated in FIG. 7A, a layer 762 of a first polymer material can be deposited, as discussed herein, on the mandrel 760 as a predefined pattern 766. In one embodiment, the predefined pattern 766 can be applied using one or more of a spray coating techniques, including ink-jet coating and/or printing techniques.

For the various embodiments, the predefined pattern 766 includes a layer having different thicknesses of the layer 762 at different portions along the mandrel 760. For example, in one embodiment a series of additional "dots" of the first polymer can be added to the top of the layer 762 to form the predefined pattern 766. Other shapes, patterns and/or configurations besides dots can be used with and/or for the predefined pattern 766.

Figure 7B:
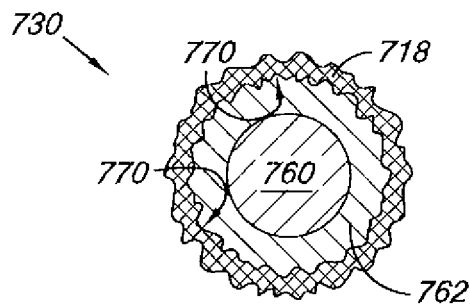

The layer 762 with its predefined pattern 766 can then be fed through the apparatus, as discussed herein, to transform at least a portion of the polymer layer 762 into the hardened zone 718. In one embodiment, the ion and implant energy used with the plasma and implanting electrodes can be selected so that only the portion of the polymer layer 762 from the exterior surface toward the mandrel 760 is transformed (e.g., carbonized) into the hardened layer 718. As illustrated in FIG. 7B, the result is a region of the polymer layer 762 positioned between the hardened layer 718 and the mandrel 760.

In addition, the apparatus 733 transforms a uniform thickness of the polymer layer 762 into the hardened zone 718. In one embodiment, transforming the uniform thickness of the polymer layer 762 into the hardened zone 718 forms pockets or divots 770 in the hardened layer 718 that mirror the predefined pattern 766. As a result, the hardened layer 718 has a pattern that is a scaled negative cast of the predefined pattern 766 applied to the polymer layer 762.

Figure 7C:
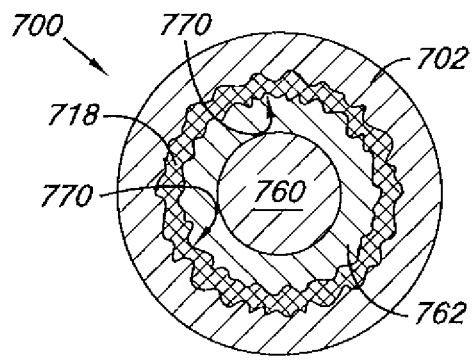

FIG. 7C next illustrates the hardened layer 718 being coated with one or more layers of the same polymer used to form the polymer layer 762 and/or a different polymer to form the polymer elongate body 702 of the catheter 700. The polymer(s) used in the coating process can include those provided herein. Alternatively, other polymer and/or non-polymer materials can be used in coating the hardened zone 718. In one embodiment, the coating process can be applied through one or more processes discussed herein.

Figure 7D:
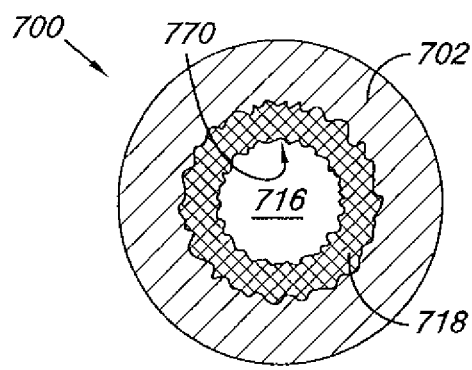

A solvent can then be used to dissolve the first polymer material of the layer 762 to both expose the hardened zone 718 with its predefined pattern and release the mandrel 760 from the catheter 700, as illustrated in FIG. 7D). Selection of a suitable solvent will depend upon the polymer(s) used in forming the polymer layer 762.

Figure 8A:
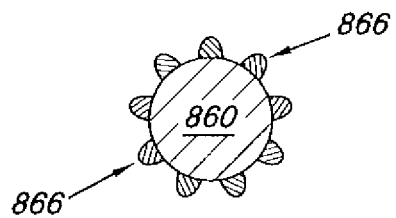
FIGS. 8A-8D illustrate the formation of a catheter having a hardened zone according to one embodiment of the present disclosure.

FIGS. 8A-8D provide a further illustration of the catheter 800 according to the present disclosure. As discussed herein, the catheter 800 illustrates an embodiment in which the hardened zone 818 is formed as a non-uniform discontinuous layer. As illustrated in FIG. 8A, a predefined pattern 866 of the first polymer can be sprayed or printed onto the mandrel 860. Examples of the predefined pattern 866 include, but are not limited to dots, lines, geometries, curves, and random patterns, among others. Use of more than one pattern is possible.

Figure 8B:
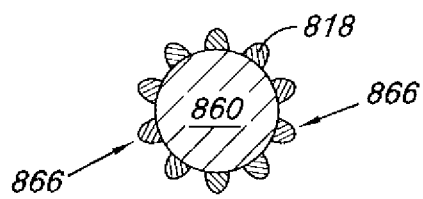
Figure 8C:
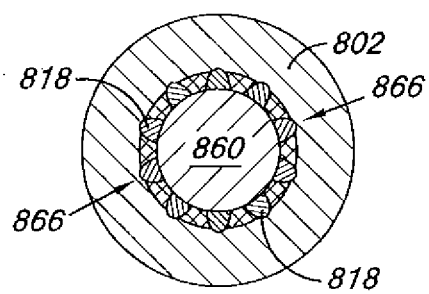

The mandrel 860 with the predefined pattern 866 of the first polymer can then be fed through the apparatus, as discussed herein, to transform the predefined pattern 866 of the first polymer into the hardened zone 818, as illustrated in FIG. 8B. The mandrel 860 with the hardened zone 818 with the predefined pattern 866 can then be being coated with one or more layers of the same polymer used to form the polymer layer 862 and/or a different polymer to form a sacrificial polymer layer 884 between the predefined pattern(s) 880 of the hardened zone 818, as illustrated in FIG. 8C.

The mandrel 860 with the hardened zone 818 in the predefined pattern 866 and the sacrificial polymer 884 can then be coated with the second polymer to form the polymer elongate body 802 of the catheter 800. The polymer(s) used in the coating process can include those provided herein. Alternatively, other polymer and/or non-polymer materials can be used in coating the hardened zone 818. In one embodiment, the coating process can be applied through one or more processes discussed herein.

Figure 8D:
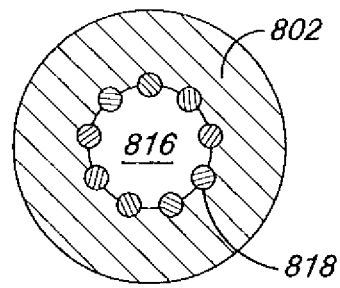

A solvent can then be used to dissolve the sacrificial polymer 884 material of the layer 862 to both expose the predefined pattern 866 of the hardened zone 818 extending from the lumen surface of the polymer elongate body 802 and to release the mandrel 860 from the catheter 800, as illustrated in FIG. 8D. Selection of a suitable solvent will depend upon the polymer(s) used in forming the sacrificial polymer layer.

While the present invention has been shown and described in detail above, it will be clear to the person skilled in the art that changes and modifications may be made without departing from the spirit and scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled. In addition, one of ordinary skill in the art will appreciate upon reading and understanding this disclosure that other variations for the invention described herein can be included within the scope of the present invention.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method of forming a catheter, comprising:
   depositing a first polymer material on a mandrel, wherein the depositing includes forming a non-uniform pattern of the first polymer material;
   forming a hardened zone in at least a portion of the first polymer material on the mandrel;
   depositing a second polymer material over the hardened zone to form the catheter;
   dissolving the first polymer to expose the hardened zone having the non-uniform pattern; and
   removing the mandrel from the catheter.

2. The method of claim 1, where forming the hardened zone includes exposing the first polymer material to ions of a plasma to carbonize the first polymer material.

3. The method of claim 2, where exposing the first polymer material to ions of the plasma carbonizes all of the first polymer material to form the hardened zone.

4. The method of claim 2, where exposing the first polymer material to ions of the plasma carbonizes a portion of the first polymer material on the mandrel to form the hardened zone.

5. The method of claim 4, including dissolving the first polymer material to expose the carbonized layer of the hardened zone and release the mandrel from the catheter.

6. The method of claim 1, where removing the mandrel from the catheter include axially stretching the mandrel to separate the mandrel from the catheter.

7. The method of claim 1, where depositing the first polymer material on a mandrel includes coating the mandrel with 2 to 400 nanometers of the first polymer.

8. The method of claim 1, where forming the hardened zone in at least a portion of the first polymer material on the mandrel includes using the mandrel as a cathode in forming a plasma.

9. The method of claim 1, where depositing the second polymer material over the hardened zone includes depositing a different type of polymer than the first polymer.

10. The method of claim 1, where depositing the second polymer material over the hardened zone includes depositing the second polymer material in an extrusion process.

11. The method of claim 1, including using a solvent to release the mandrel from the catheter.

12. The method of claim 11, where using the solvent includes dissolving the first polymer material between the mandrel and the hardened zone.

13. The method of claim 1, where depositing the first polymer material on a mandrel to form the non-uniform pattern includes forming a predefined pattern of the first polymer material.

14. The method of claim 13, where forming the hardened zone includes transforming a uniform thickness of the first polymer of the predefined pattern from an exterior surface of the first polymer towards the mandrel.

15. The method of claim 14, dissolving the first polymer material to expose the hardened zone having the predefined pattern.

\* \* \* \* \*